United States Patent
Carvalho et al.

(10) Patent No.: US 6,395,931 B1
(45) Date of Patent: May 28, 2002

(54) MALONIC ACID AND ESTERS THEREOF

(75) Inventors: Otavio Vianna Carvalho; Ronaldo Mendonca Mansur; Sandro da Silva Aguiar; Jane Hitoni Fujiyama; Antonio Luiz Ribeiro de Castro, all of Maceio (BR)

(73) Assignee: Trikem S.A., Salvador (BR)

( * ) Notice: Subject to any disclaimer, the term of this patent is extended or adjusted under 35 U.S.C. 154(b) by 0 days.

(21) Appl. No.: 09/423,797

(22) PCT Filed: Aug. 10, 1998

(86) PCT No.: PCT/BR98/00058
§ 371 (c)(1),
(2), (4) Date: Jan. 14, 2000

(87) PCT Pub. No.: WO99/08988
PCT Pub. Date: Feb. 25, 1999

(30) Foreign Application Priority Data

Aug. 13, 1997 (BR) .............................. 9709357

(51) Int. Cl.[7] .................. C07C 55/00; C07C 69/34; C07C 69/52
(52) U.S. Cl. ...................... 562/590; 560/190
(58) Field of Search ........................ 562/590

(56) References Cited

U.S. PATENT DOCUMENTS

| | | | | |
|---|---|---|---|---|
| 2,337,858 A | | 12/1943 | Stoesser | 260/435 |
| 2,459,144 A | * | 1/1949 | Christie | 260/485 |

FOREIGN PATENT DOCUMENTS

| | | | | |
|---|---|---|---|---|
| DE | 953874 | * | 12/1956 | |
| GB | 1240410 | * | 11/1969 | C07C/55/14 |
| JP | 51143612 | | 12/1976 | |
| JP | 53127411 | | 11/1978 | |
| JP | A-597135 | | 1/1984 | |
| JP | A-597136 | | 1/1984 | |
| NL | 6613168 | * | 3/1968 | |

OTHER PUBLICATIONS

M. L. Henry, "Sur le dinitrile malonique", Compte Rendus, vol. 102, (1886), pp. 1394–1397.*

Kiyoshi Matsumoto et al, "Reaction of Pyridinium Bis-(methoxycarbony)methylid with Diphenylcyclopropenethione: A Revised Structure for One of the Products" Heterocyles, vol. 23(8), (1985), pp. 2041–2043).*

"On the Conversion of Cyanacetic Ester to Malonic Ester" Phelps et al. Chemical Abstracts 3, p. 1533 (1909).*

Derwent Publication Ltd., London, GB; AN 84–046207 XP–002089183.

Derwent Publication Ltd., London, GB: AN 84–046206 XP–002089184.

Organic Syntheses, Collective vol. 2, Revised Edition of Annual vol. X–XIX Edited by A.H. Blatt; Taken from Reg. No. 09/971,211; Published by John Wile & Sons; pp. 376–378.

* cited by examiner

Primary Examiner—Gary Geist
Assistant Examiner—Zachary C. Tucker
(74) Attorney, Agent, or Firm—Birch, Stewart, Kolasch & Birch, LLP

(57) ABSTRACT

A process for preparing malonic acid from the hydrolysis of cyanoacetic acid in the presence of aqueous hydrochloric acid, the process conditions being such that they allow high yields in malonic acid product. The product of said acid hydrolysis is a mixture of malonic acid and ammonium chloride by-product; the mixture is concentrated, the ammonium chloride by-product is separated by dissolution with an oxygen solvent and isolated. Alternatively, said concentrated mixture is dissolved with a primary or secondary esterifying alcohol in $C_1$–$C_{10}$, the resulting mixture being esterified, while the ester product is purified by distillation under reduced pressure, the molar yields and purity of the ester product being high.

19 Claims, 1 Drawing Sheet

MALONIC ACID AND ESTERS THEREOF

This application is the national phase under 35 U.S.C. § 371 of PCT International Application No. PCT/BH98/00058 which has an International filing date of Aug. 10, 1998, which designated the United States of America.

FIELD OF THE INVENTION

The present invention relates to a process for preparing malonic acid and its esters from cyanoacetic acid which is hydrolyzed in the presence of aqueous hydrochloric acid. More specifically, the present invention relates to a high-yield process for obtaining malonic acid as well as its respective esters in $C_1$–$C_{10}$ from cyanoacetic acid, specially to the esters derived from secondary alcohols, such as isopropyl alcohol.

BACKGROUND INFORMATION

Malonic acid and specially its esters are widely used industrial products which find application mainly in the fields of pharmaceuticals, agricultural products and cosmetics.

Malonic acid production from the hydrolysis of cyanoacetic acid in the presence of strong acids such as sulfuric acid or bases is well-known.

Alternatively, malonic acid esters may be prepared from the acid hydrolysis of cyanoacetic acid in the presence of the alcohol which will generate the desired ester.

Esters of malonic acid may also be obtained from the classical route which involves the esterification of pure malonic acid.

Another well-known process utilizes the carbonylation of chloracetic acid in the presence of alcohols in order to prepare the esters of malonic acid.

Japanese patents JP 51-143612 A, JP 59-007135, JP 59-007136 A and U.S. Pat. No. 2,337,858 teach that malonic acid esters may be prepared from procedures which involve high consumption of sulfuric acid, the synthesis of malonic acid per se being not reported.

The process taught in *ORGANIC SYNTHESES COLLECTION—VOLUME II*, A. H. BLATT Ed., JOHN WILEY, New York, 1943, page 376 is based on the alkaline hydrolysis of cyanoacetic acid so as to obtain the salt of malonic acid which then is made to react with calcium chloride in order to form calcium malonate. This salt is made into the free salt by means of acid hydrolysis and then extracted with an organic solvent.

Japanese patent 53-127411 teaches the preparation of malonic acid through the alkaline hydrolysis of cyanoacetamide with calcium hydroxide and then acidification with sulfuric acid.

However, the open literature does not present processes leading to a high-yield hydrolysis of cyanoacetic acid as well as the application of such hydrolysis to ester derivatives of secondary alcohols from the mixture of malonic acid contaminated with hydrolysis by-products such as ammonium salts, such process being described and claimed in the present application.

SUMMARY OF THE INVENTION

The process for preparing malonic acid and its esters according to the present invention comprises:
Preparation of the Concentrated Mixture
Malonic acid is prepared through the hydrolysis of cyanoacetic acid in the presence of an at least stoichiometric amount of aqueous hydrochloric acid yielding a mixture which is the desired product malonic acid and the by-product ammonium chloride besides small amounts of acetic acid. A concentrated mixture is obtained when malonic acid and ammonium chloride are separated from water, acetic acid and the excess hydrochloric acid present in the medium;
Isolation of Malonic Acid
The concentrated mixture of malonic acid and ammonium chloride is purified by dissolving with an oxygen organic solvent the malonic acid product being then separated from the ammonium chloride by-product so as to obtain malonic acid purified and isolated through evaporation of the oxygen organic solvent;
Preparation of Malonic Esters
The concentrated mixture of malonic acid and ammonium chloride is purified by dissolving with the esterifying alcohol, the malonic acid-esterifying alcohol mixture being separated from the ammonium chloride by-product and esterified in the presence of a Brönsted acid catalyst and an azeotrope-forming organic co-solvent, under heating, in order to obtain the desired ester product.

Therefore, the present process for preparing malonic acid comprises the hydrolysis of cyanoacetic acid in the presence of an at least stoichiometric amount of aqueous hydrochloric acid in a concentration between 5 and 37% by weight, yielding a mixture which is the desired product malonic acid and by-product ammonium chloride, which should be separated from water, excess hydrochloric acid and acetic acid by-product in order to obtain a concentrated mixture which is purified by dissolving with an oxygen organic solvent under suitable conditions of pressure and temperature, the desired product being then separated from the ammonium chloride by-product so as to obtain malonic acid which is purified and isolated by evaporating the oxygen organic solvent.

And the process for preparing the malonic esters according to the present invention comprises the hydrolysis of cyanoacetic acid in the presence of an at least stoichiometric amount of aqueous hydrochloric acid in a concentration in the range of 5 to 37% by weight, yielding a mixture which is the desired product malonic acid and by-product ammonium chloride, which should be separated from water, excess hydrochloric acid and acetic acid by-product in order to obtain a concentrated mixture, such mixture being purified by dissolving with the esterifying alcohol, the mixture malonic acid-esterifying alcohol being separated from the ammonium chloride by-product and esterified in the presence of a Brönsted acid catalyst and a ternary azeotrope-forming organic solvent, under heating, so as to obtain the desired ester product.

Thus, the present invention provides a process for preparing malonic acid and its esters in high yields as a consequence of the hydrolysis under mild conditions in the presence of aqueous hydrochloric acid, such conditions reducing the decarboxylation of the desired product, therefore lowering the amount of acetic acid by-product of the reaction.

The present invention provides further a process for preparing malonic acid of low water content and low concentration in residual mineral acid as a consequence of the use of volatile hydrochloric acid. The volatile hydrochloric acid may be recovered on evaporating, then concentrated and recycled to the process. The relatively low concentration of hydrolyzing agent as well as the low temperature in the medium during evaporation leads to high yields.

Still, the present invention provides a process for preparing malonic acid esters in high yield as a consequence of running the esterification in the presence of catalytic amounts of a Brönsted acid, so as to minimize the decarboxylation besides the dehydration of alcohol, particularly secondary alcohols.

DETAILED DESCRIPTION OF THE PREFERRED MODES

Figure 1:
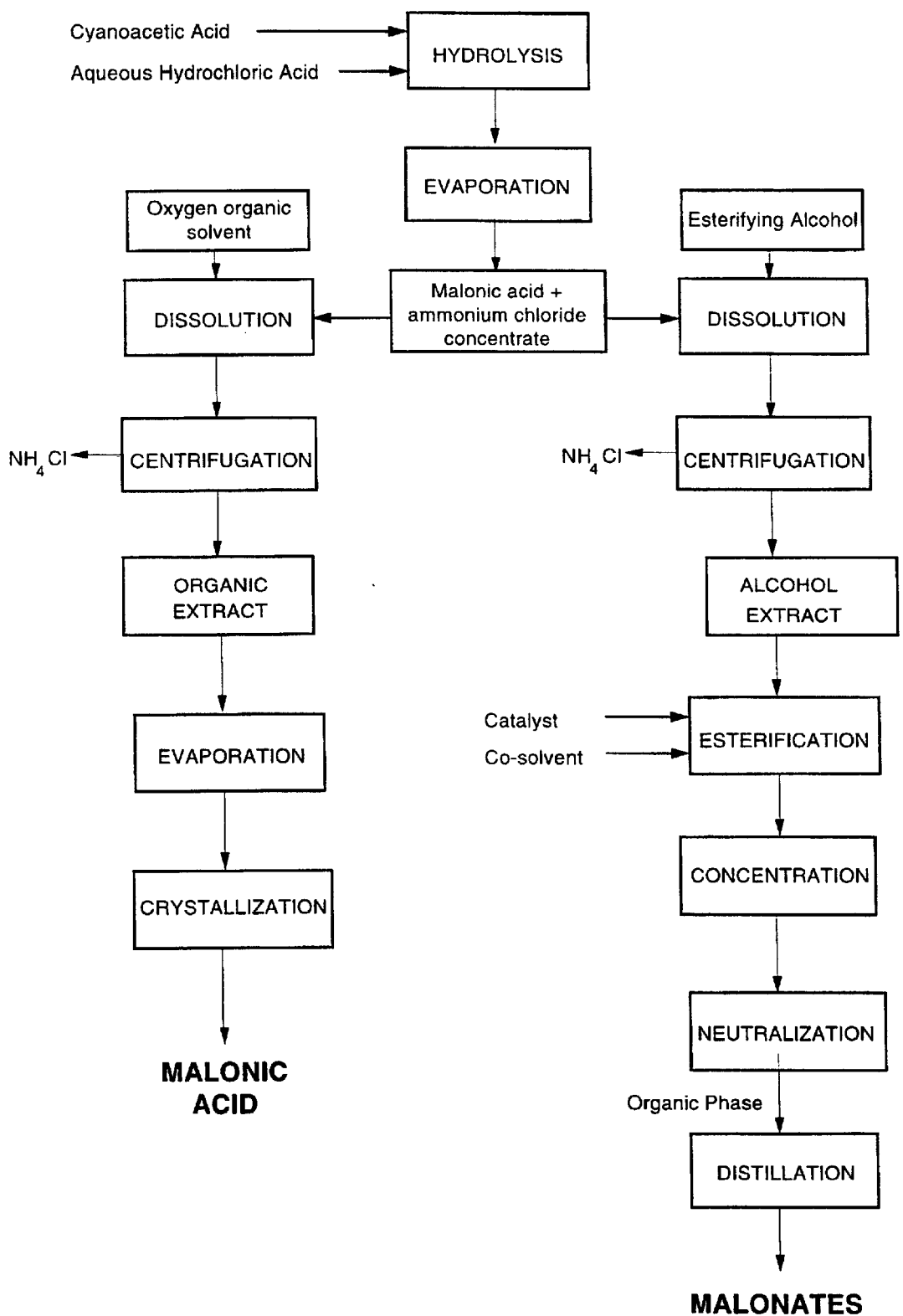
FIG. 1 attached is a flowchart which illustrates the preferred modes of the present invention for preparing malonic acid and esters thereof.

Throughout the present specification, the expression below has the following meaning:

Mild Hydrolysis: it is the hydrolysis effected according to the present process, which uses as mineral acid, hydrochloric acid exclusively in a concentration between 5 and 37%. A hydrolysis is said mild when the molar amount of acetic acid formed as by-product of the cyanoacetic acid hydrolysis is lower than 4%. In state-of-the-art processes which use strong mineral acids as sulfuric acid or bases for hydrolyzing cyanoacetic acid such percentage attains figures which are significantly higher than 4%. The amounts of acetic acid as by-product of the reaction mean losses in desired product, such losses being minimized by using the process of the present invention for preparing malonic acid.

Thus, one preferred mode of the invention comprises preparing malonic acid in high yields through the mild hydrolysis of cyanoacetic acid in the presence of an at least stoichiometric amount of aqueous hydrochloric acid.

Schematically, the process for preparing malonic acid according to the present invention may be represented by the Equation (1) below:

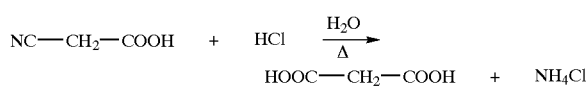

(1)

Thus, according to the concept of the present invention, the mild hydrolysis comprises the reaction of cyanoacetic acid with an at least stoichiometric amount of hydrochloric acid of concentration between 5 and 37% by weight, preferably between 10 and 37% by weight.

The advantages of the preferred use of hydrochloric acid as the hydrolyzing agent are as follows:

reduced decarboxylation of the desired product, malonic acid, which increases the overall yield of the process;
the volatile hydrochloric acid may be recovered on evaporating, then concentrated and recycled to the process;
the relatively low temperature and low concentration of hydrolyzing agent throughout the evaporation effected for removal of water existing in the medium leads to high yields in desired product.

The mild hydrolysis of cyanoacetic acid according to the present invention occurs in a closed reactor vessel at a temperature of at least 50° C., preferably of from 60 to 100° C., especially of from 70 to 90° C., while the pressure is between 0.5 to 10 bar, preferably of from 1 to 7 bar.

The molar ratio of hydrochloric acid to cyanoacetic acid may be situated between 1.0 and 5.0, preferably 1.3 to 2.0.

In spite of the fact that the reaction easily occurs for stoichiometric amounts of cyanoacetic acid and hydrochloric acid, in order to increase the reaction rate preferably a molar excess of at least 30% in hydrochloric acid is used. The excess hydrochloric acid should be withdrawn and recycled after the hydrolysis reaction.

The range of useful temperatures and molar ratios of hydrochloric acid to cyanoacetic acid are interrelated and determine the reaction period. Thus, for lower temperatures, such as 50° C., the reaction will either proceed for relatively higher molar ratios of hydrochloric acid to cyanoacetic acid, or for longer reaction periods. On the contrary, for higher reaction temperatures, reduced molar ratios or reaction periods may be used.

As a result from the hydrolysis of cyanoacetic acid, the reaction medium contains the desired product (malonic acid) admixed with the ammonium chloride by-product, excess hydrochloric acid, acetic acid formed from the decarboxylation of malonic acid and water from the hydrochloric acid added. Most of that water, of the excess hydrochloric acid and the small amount of acetic acid formed should be withdrawn from the reaction medium, for example by evaporation or any other well-known method such as distillation.

It was found that for withdrawing water during the formation of the concentrated mixture, the addition of further organic solvents is not critical in order to isolate the malonic acid product of the reaction. However, water may be withdrawn by using a well-known procedure such as by adding a solvent such as benzene or toluene, which form azeotropic mixtures with water.

Water, excess hydrochloric acid and formed acetic acid are withdrawn by evaporating between 40 and 1330 mbar absolute pressure, preferably between 133 and 400 mbar. Preferably, evaporation is effected in the reactor vessel itself. Alternatively, evaporation may be effected in a suitable evaporator such as agitated thin film, flash dryer or spray dryer.

After evaporation, the resulting solid comprises malonic acid, ammonium chloride, small amounts of water and hydrochloric acid.

The dissolution of malonic acid is effected by means of oxygen organic solvents such as:

ketones in $C_3$–$C_8$;
acyclic ethers in $C_2$–$C_{10}$ or cyclic ethers;
esters in $C_2$–$C_6$.

After dissolution of the malonic acid product, the ammonium chloride by-product is separated through classical solid-liquid separation means such as centrifugation or filtration.

One of the ways to effect the final isolation of malonic acid is to withdraw the oxygen solvents mentioned hereinbefore, by concentrating the extract which is done by evaporating and crystallizing the desired product at a temperature range between –20 and 35° C., more preferably –5 to 10° C., followed by filtration of the centrifuged suspension. The thus obtained filtrate is again pre-concentrated and the crystallization procedure is repeated in the above-mentioned conditions. The filter cakes obtained after the two crystallizations lead, after drying, to the desired malonic acid in higher than 90% yield and high purity. The mother liquor is recycled to be further used with another stream of oxygen solvent to be employed with another filter cake, so as to secure the recovery of the remaining dissolved malonic acid so as to attain higher than 96 mole % yield.

Another preferred mode of the present invention is directed to the preparation of malonic acid esters from the concentrated mixture of malonic acid and ammonium chloride obtained as described hereinbefore.

The dissolution of malonic acid is effected with the aid of the esterifying alcohol. As esterifying alcohols are used primary and secondary alcohols in $C_1$–$C_{10}$.

The ammonium chloride by-product is separated from the malonic acid by means of classical methods for solid-liquid separation such as centrifugation or filtration. The resulting malonic acid-alcohol mixture is then directed to the esterification process.

Schematically, the preparation of malonic acid esters according to the present invention may be represented by equation (2) below:

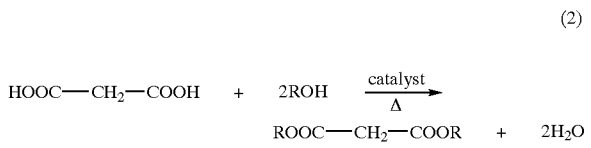

(2)

Another advantage of the present invention as compared to the state-of-the-art technique is that the present process for preparing malonic acid esters allows that secondary alcohol esters be prepared under optimum conditions, not found in state-of-the-art processes. On the contrary, those processes utilizing strong mineral acids such as sulfuric acid in high concentrations so as to effect the hydrolysis of cyanoacetic acid and the esterification in one single step eventually promote the dehydration of the secondary alcohol, so as to yield the corresponding alkene. In the inventive process, however, the esterification reaction is effected in the presence of catalytic amounts of mineral acids, this avoiding the dehydration of the secondary alcohol.

Alcohols, exception made to methyl alcohol, act as solvents as well to promote the withdrawal of the water formed during the esterification reaction. They are used in the binary azeotropic distillation and may also be used with co-solvents to form ternary azeotropes.

The catalysts for the esterification reaction are not critical and may comprise the following substances: chlorosulfonic acid, methanosulfonic acid, p-toluenesulfonic acid, hydrochloric acid, sulfuric acid and other Brönsted acids More preferably sulfuric acid in molar amounts between 0.005 and 0.5 mole, preferably from 0.07 to 0.15 mole per mole of malonic acid. These amounts are significantly lower than those stated in Japanese patents JP 59-007136A and JP 59-00135A which employ molar ratios of from 3 to 4 times the number of moles of cyanoacetic acid.

There are no restrictions whatsoever as regards the molar ratio of alcohol to each mole of malonic acid. This ratio is at least the stoichiometric amount, that is, 2 moles of alcohol to I mole of malonic acid.

The esterification reaction may be processed under pressures which vary between 67 and 1100 mbar more preferably in the range of 147 mbar to 507 mbar. The composition of binary or ternary azeotrope as well as its distillation range are directly linked to the pressure conditions of the reaction, the characteristics of the alcohol employed and the kind of co-solvent, if used.

After the reaction is complete the medium is neutralized with aqueous solutions of inorganic bases such as sodium carbonate in concentrations which may oscillate between 5 and 30% by weight. Solid bases may as well be used, as well as solutions/suspensions in the esterifying alcohol.

In order to effect the final distillation of the ester product, the malonate-rich organic phase is separated by decanting, according to conventional methods.

The distillation of the ester product is effected either continuously or in batch and yields the ester product in high yield and purity of at least 99.0 mole %.

It should be borne in mind that although the present invention is being described as being specially directed to the preparation of malonic acid and the esters thereof, the principles of same apply as well to other cyano-carboxylic acids, such as for example cyano propionic acid, cyano butanoic acid and their respective esters of commercial interest.

The present invention is now explained in more detail by means of the following Examples, which should not be construed as limiting same.

EXAMPLE 1

Preparation of Malonic Acid:

The process for preparing malonic acid comprises acid hydrolysis with aqueous hydrochloric acid, evaporation, dissolution, centrifugation and crystallization, as illustrated in FIG. 1 attached.

Thus, 85.06 g of cyanoacetic acid (1 mole) were charged in an autoclave made of Hastelloy-C having I liter volumetric capacity, then 457.69 g of HCl 30.99% by weight were added, corresponding to 3.88 moles of HCl relative to cyanoacetic acid. The reaction medium was kept under agitation at 350 rpm and heated at a temperature of 70±5° C. and at absolute pressure above 2.0 bar. After a 4 hour reaction and cooling to room temperature the pressure in the autoclave was relieved.

The liquid phase of the reaction medium was evaporated under reduced pressure, yielding a condensate containing the molar excess of HCl, 2.1 g acetic acid and 156.58 g of a wet solid the analysis of which showed the following composition, by weight:

| Component | Weight % |
|---|---|
| Water | 1.33 |
| Cyanoacetic acid | 0.1 |
| Hydrochloric acid | 0.69 |
| Malonic acid | 64.12 |
| Ammonium chloride | 33.42 |

To this solid were added 160.7 g of tetrahydrofuran (THF). The resulting suspension was kept under agitation at room temperature for 40 minutes and then insoluble ammonium chloride was filtered. The filtrate was concentrated by evaporating 116.1 g of THF and left to crystallize at a temperature of 10±5° C. The suspension was filtered yielding 75.4 g of liquid phase containing 36.8 weight % of malonic acid, corresponding to 27.74 g and a white solid which after drying weighed 69.6 g. By analysis it was ascertained that the so-obtained malonic acid was 99.6 mole % pure.

Since the mass of malonic acid in the filtrate is 27.74 g, the overall yield of this reaction was 93.3%. The 27.74 g mass is isolated by evaporating the THF under reduced pressure. Analysis of ammonium chloride has shown 6 weight % of malonic acid in this residue, corresponding to 3.3 g of malonic acid, which may be recovered by washing this solid with the liquid stream from the crystallization, the final yield in malonic acid being 96.5 mole %.

EXAMPLE 2

Preparation of Malonic Acid:

127.59 g of cyanoacetic acid (1.5 mole) were charged into an autoclave made of Hastelloy-C of volumetric capacity of 1 liter, then 235.48 g of HCl solution of 30.99 weight % were added, corresponding to 1.99 moles of HCl to each mole of cyanoacetic acid. The reaction was kept under agitation at 400 rpm and heated at a temperature of 80±5 ° C. and at absolute pressure of 1.3 bar. After a 5 hour reaction and cooling up to room temperature the pressure was relieved.

The liquid phase was evaporated under reduced pressure yielding a condensate containing the molar excess of HCl and 2.6 g of acetic acid besides 246.5 g of a wet solid which showed the following analysis, by weight:

| Component | Weight % |
| --- | --- |
| Water | 4.2 |
| Cyanoacetic acid | 0.1 |
| Hydrochloric acid | 1.69 |
| Malonic acid | 61.4 |
| Ammonium chloride | 32.55 |

To such solid 856.05 g of methyl-tert-butyl ether (MTBE) were added. The so-formed suspension was kept under agitation at room temperature for 40 minutes, and then insoluble ammonium chloride was filtered. The filtrate was concentrated by evaporating 688.9 g of MTBE and left to crystallize at a temperature of 10±5° C. The suspension was filtered yielding 202.8 g of liquid phase having 17.6 weight % of malonic acid, corresponding to a mass of 34.5 g and a solid which after drying weighed 115.8 g. By analysis it was ascertained that the so-obtained malonic acid was 99.8% pure.

The mass of 34.5 g of malonic acid dissolved in the filtrate means that the overall yield of the reaction is 96.19%. The 34.5 g mass is isolated by evaporating said MTBE solvent under reduced pressure. The ammonium chloride analysis indicated 2.6 weight % malonic acid in this residue, corresponding to 1.4 g of malonic acid, which may be recovered by washing the solid with the liquid stream from the crystallization, the final yield attaining 97.1 mole %.

EXAMPLE 3

Preparation of Malonic Acid:

127.59 g of cyanoacetic acid (1.5 moles) were charged into an autoclave made of Hastelloy-C having a volumetric capacity of 1 liter, then 221.2 g of HCl 33.0 weight % solution were added, corresponding to 2.0 moles. The reaction was kept under agitation at 400 rpm and heated to a temperature of 75±5 ° C. and at a pressure of 1.5 bar. After a 5 hour reaction and cooling up to the room temperature the pressure of the autoclave was relieved.

The liquid phase was evaporated under reduced pressure, yielding a condensate containing the molar excess of HCl, 1.8 g of acetic acid and 236.03 g of a wet solid which showed the following composition by weight:

| Component | Weight % |
| --- | --- |
| Water | 1.0 |
| Cyanoacetic acid | 0.2 |
| Hydrochloric acid | 0.2 |
| Malonic acid | 64.7 |
| Ammonium chloride | 34.0 |

To this wet solid 2259.0 g of methyl-isobutyl-ketone (MIBK) were added. The resulting suspension was kept under agitation at room temperature for 40 minutes, then the insoluble ammonium chloride was filtered. The filtrate was concentrated by evaporating 2135.1 g of MIBK and left to crystallize at a temperature of 10±5 ° C. The suspension was filtered yielding 110.1 g of liquid phase having 5.5 weight % of malonic acid, corresponding to 6.08 g and a white solid which after drying weighed 147.0 g. By analysis it was ascertained that the so-obtained malonic acid was 99.6 mole % pure.

The mass of 6.08 g of malonic acid dissolved in the filtrate means that the overall yield of the reaction is 97.7%. The 6.08 g mass is isolated by evaporating the MIBK solvent under reduced pressure. The ammonium chloride analysis indicated 0.75 weight % malonic acid in this residue, corresponding to 0.39 g of malonic acid, which may be recovered by washing the solid with the liquid stream from the crystallization, the final yield attaining 98.0 mole %.

CONTROL EXAMPLE 1

This Control Example shows that hydrolysis in the presence of sulfuric acid leads to low yields in malonic acid. This is based on the teachings of Japanese patent 59-007136A.

Thus, 85.06 g of cyanoacetic acid (1.00 mole) were charged into a jacketed glass reactor of 1 liter volumetric capacity. The 54.00 g (3.00 moles) of water were added, under agitation of 290 rpm, at room temperature (26° C.).

2.00 moles sulfuric acid 97 weight % (202.14 g) were then pumped into the reactor at such a rate that the internal temperature would not outweigh 45° C. (period of time for sulfuric acid addition: 30 minutes). When sulfuric acid addition was complete, the contents of the reactor were heated up to the range of 83 to 84° C. for 8 hours up to point where cyanoacetic acid was completely spent.

As a result, 26.02 weight % of malonic acid were formed in the reaction mixture (88.7 g), this corresponding to a molar yield of 85.36% in raw malonic acid.

Further, the reaction medium contained also 4.71 mole % acetic acid as well as 9.83 mole % of an amide.

It is therefore easily seen the low yield in malonic acid as well as the relatively high amount of by-products (acetic acid and amide) resulting from the use of state-of-the-art techniques. The high amount of sulfuric acid in the reaction medium is a further drawback for the purification step.

EXAMPLE 4

Preparation of Diethyl Malonate:

The process comprises the steps of acid hydrolysis, evaporation, dissolution with alcohol, separation of ammonium chloride (by filtration, centrifugation or any equivalent technique), esterification, neutralization and distillation, as schematically illustrated in FIG. 1 attached.

Thus, 52.1 1 g of cyanoacetic acid (0.61 moles) were charged into an autoclave made of Hastelloy-C having volumetric capacity of 1 liter, then 135,43 g of HCl 33.0 weight % solution were added, corresponding to 1.22 moles. The reaction was kept under agitation at 420 rpm and heated at a temperature of 75±5° C. and at absolute pressure of 1.4 bar. After a 5 hour reaction and cooling to the room temperature the pressure in the autoclave was relieved.

The liquid phase was evaporated under reduced pressure, yielding a condensate containing the molar excess of HCl with 0.73 g of acetic acid and 96.06 g of a wet solid which showed the following composition by weight:

| Component | Weight % |
| --- | --- |
| Water | 1.3 |
| Cyanoacetic acid | Not found |
| Hydrochloric acid | 0.1 |
| Malonic acid | 64.7 |
| Ammonium chloride | 33.9 |

These figures lead to the conclusion that the yield in raw malonic acid in this first step was 97.9%.

To this wet solid 263.1 g of ethyl alcohol (5.69 moles) were added. The resulting suspension was kept under agitation at room temperature for 40 minutes, then the insoluble ammonium chloride was filtered. No malonic acid was found admixed to ammonium chloride. To the filtrate 8.5 g of methanesulfonic acid (0.087moles) were added, the mixture being then transferred to a glass reactor. The reaction was run in a jacketed reactor of 500 ml of volumetric capacity coupled to a distillation kit. After heating for 2 hours at an internal temperature of 81° C. the distillation of a binary azeotropic mixture of ethyl alcohol and water was started, at a temperature of 78.5° C. After a 3 hour distillation, 125.7 g of toluene as co-solvent were added to the reaction medium, with the ensuing distillation of a ternary azeotropic mixture made up of toluene, ethyl alcohol and water, this mixture being separated in a different decanter. Due to the excess ethyl alcohol in the medium, no phase separation occurred and therefore the recycle of this stream (toluene/ethyl alcohol) to the reaction medium was not required in order to complete the esterification of malonic acid. After a 8 hour reaction a chromatographic test did not indicate the presence of malonic acid. The diethyl-malonate-rich reaction medium was then concentrated under reduced pressure, at a manometric pressure between −927 and −283 mbar. The concentrate was then neutralized with the aid of 1 50.0 g of a 5 weight % aqueous solution of sodium hydroxide so as to form two liquid phases which were separated in a decanter. So, 171.8 g of aqueous phase were obtained containing 0.89 weight % of diethyl malonate, which corresponds to a mass of 1.53 g which in turn may be recovered by extracting with toluene and further recycle to the next batch. The efficacy of such procedure for recovering the product attained 97% which means a recovery of 1.48 g of diethyl malonate.

The organic phase weighed 104.5 g and its composition was as follows, by weight:

| Component | Weight % |
| --- | --- |
| Water | 1.0 |
| Ethyl alcohol | 2.5 |
| Toluene | 11.0 |
| Ethyl acetate | 0.20 |
| Diethyl malonate | 86.0 |

The diethyl malonate product was purified by fractional distillation, in a batch, under reduced pressure, the first stream to be distilled containing substances of lower boiling point. The distillation of the desired product occurred at an absolute pressure of 40 mbar and internal temperature of 133° C., the diethyl malonate being distilled at 108–109° C. The yield in desired ester product was 90.0 g of purity 99.7 mole %, this meaning that the yield based on cyanoacetic acid was 91.9 mole %. If the recovery of 1.48 g from the extraction of the aqueous phase is considered, the overall yield is 93.4 mole %.

EXAMPLE 5

Preparation of Di-butyl Malonate:

42.14 g of cyanoacetic acid (0.495 moles) were charged to an autoclave made of Hastelloy-C having a volumetric capacity of 1 liter, then 121.66 g of a 30 weight % solution of HCl were added, corresponding to 1.0 mole. The reaction was kept under agitation at 420 rpm and heated to a temperature of 77° C., the absolute pressure being 1.3 bar. After a 5 hour reaction the mixture of malonic acid and ammonium chloride was isolated according to the procedures described in the preceding examples yielding a condensate with the molar excess of HCl with 0.59 g of acetic acid and 80.02 g of a wet solid which by analysis showed the following composition, by weight:

| Component | Weight % |
| --- | --- |
| Water | 2.7 |
| Cyanoacetic acid | not found |
| Hydrochloric acid | 1.2 |
| Malonic acid | 63 |
| Ammonium chloride | 33.1 |

These results indicate that in the first step the yield in raw malonic acid was 97.92%.

To the above wet solid 340.0 g of n-butyl alcohol were added, corresponding to 4.56 moles. The resulting suspension was kept under agitation at room temperature for 40 minutes for dissolving malonic acid, then insoluble ammonium chloride was filtered and washed with further 100 g of n-butyl alcohol (corresponding to 1.34 moles). After washing, analytical testing of the ammonium chloride did not indicate any malonic acid admixed to it. The liquid alcoholic streams were admixed and 7.2 g (corresponding to 0.07 mol) of concentrated sulfuric acid were added, the mixture being transferred to a glass reactor. The reaction was run in a jacketed reactor of 500 ml volumetric capacity, the reactor being coupled to a distillation device. After heating for 1 hour at an internal temperature of 84° C. and 173 mbar absolute pressure a binary azeotropic mixture made up of n-butyl alcohol and water started to distill, at a temperature of 43.2° C., the decanter showing two phases. After a 4 hour distillation period a chromatographic analysis did not show any malonic acid in the collected product. The dibutyl-malonate rich medium was then concentrated under reduced pressure at an absolute pressure between 173 and 106.4 mbar. The concentrate of the reaction was neutralized with 79 g of a 10 weight % of an aqueous solution of sodium carbonate yielding two liquid phases which were separated in the decanter.

88.4 g of aqueous phase containing 0.05 weight % of dibutyl malonate, corresponding to a mass of 0.047 g. This mass may be recovered through extraction with toluene and further recycle to the following batch. The efficacy of such procedure for recovery of the product was 98.5%, corresponding to 0.046 g of dibutyl malonate.

The organic phase weighed 103.8 g and had the following composition, by weight:

| Component | Weight % |
|---|---|
| Water | 1.9 |
| n-butyl alcohol | 4.4 |
| Dibutyl malonate | 93.7 |

Dibutyl malonate was purified by fractional distillation, in batch and under reduced pressure, n-butyl alcohol and water being distilled at first. The distillation of the desired ester product occurred at absolute pressure of 8 mbar, the ester distilling between 106 and 107° C. 95.8 g of dibutyl malonate were obtained of 99.8 mole % purity, the yield based on cyanoacetic acid being 89.3 mole %.

EXAMPLE 6
Preparation of Diisopropyl Malonate:

365.75 g of cyanoacetic acid corresponding to 4.30 moles were charged into a Hastelloy-C autoclave of 2 liters volumetric capacity, then 1,000 g of an aqueous solution of HCl 30.99% (corresponding to 8.5 moles) were added. The reaction was kept under agitation at 350 rpm and heated at a temperature of 70° C. and at an absolute pressure of 1.3 bar. After a 7 hour reaction the mixture of malonic acid and ammonium chloride was isolated according to the procedure described hereinbefore a condensate with the HCl molar excess with 3.87 g of acetic acid and 754.5 g of a wet solid which by analysis showed the following composition, by weight:

| Component | Weight % |
|---|---|
| Water | 4.8 |
| Cyanoacetic acid | 0.07 |
| Hydrochloric acid | 7.0 |
| Malonic acid | 57.6 |
| Ammonium chloride | 30.4 |

These results indicate that in the first step the yield in raw malonic acid was 97.2%.

To the above solid were added 2340.0 g of isopropyl alcohol (corresponding to 39 moles), the resulting suspension was kept under agitation for 40 minutes for dissolving malonic acid, then the insoluble ammonium chloride was separated by filtering. The analysis of ammonium chloride indicated the presence of 2.4 g of malonic acid, which may be recovered by washing the ammonium chloride residue with isopropyl alcohol and further recycle of said stream to the next batch. To the liquid alcoholic stream were then added 10.0 g of concentrated sulfuric acid, corresponding to 0.102moles, then transferring the mixture to a glass reactor. The reaction was run in a jacketed reactor of 4,000 ml volumetric capacity coupled to a device for distillation under reduced pressure. After heating for 1 hour at an internal temperature of 65° C. and 186.2 mbar absolute pressure a binary azeotropic mixture made up of ispryl alcohol and water began to distill, at a temperature of 46.5° C. After 7 hours distillation, 600 g isopropyl alcohol were added, the binary mixture being distilled under the reaction conditions set forth hereinbefore. The reaction proceeded for additional 6 hours when a further 600 g of isopropyl alcohol were added in order to have the esterification reaction completed. When 20 hours reaction were completed a chromatographic analysis test was run, which did not indicate any malonic acid in the medium. The di-isopropyl malonate-rich reaction medium was then concentrated, at an absolute pressure between 186.2 mbar and 66.5 mbar. The concentrate was then neutralized with the aid of 216.2 g of a 5 weight % aqueous solution of sodium carbonate so as to yield two liquid phases which were separated in a decanter. 242 g of aqueous phase were obtained having 0.94 weight % of di-isopropyl malonate, corresponding to a mass of 2.27 g, which may be recovered by extraction with toluene and further recycle to the next batch. The efficacy of such procedure for recovering the desired ester product was 99.0%, this corresponding to a recovery of 2.25 g of di-isopropyl malonate.

The organic phase weighed 820 g and had the following composition, by weight:

| Component | Weight % |
|---|---|
| Water | 1.9 |
| Isopropyl alcohol | 5.6 |
| Di-isopropyl malonate | 92.45 |

Diisoproyl malonate was purified by fractional distillation, in batch and under reduced pressure, isopropyl alcohol and water being distilled at first. The distillation of the desired ester product occurred at an absolute pressure of 10.6 mbar, the ester distilling at 92° C. 750.09 g of diusopropyl malonate were obtained of 99.0% purity, the yield based on cyanoacetic acid being 91.8%. On adding 2.25 g of desired product recovered from the aqueous phase, the overall yield reaches 92.1 mole %.

CONTROL EXAMPLE 2

This Example demonstrates that the state-of-the-art technique is not suitable for preparing esters from secondary alcohols, for example, as taught in Japanese patent 59-007136A. The preparation of malonic acid according to said patent is reported in Control Example 1 hereinbefore.

After the reaction medium obtained according to Control Example 1 was cooled were added, during 15 minutes, 227.46 g of isopropyl alcohol (3.80 moles) and 49.28 g of toluene (0.53 moles), the reaction medium being kept at 80° C. for 3 hours.

The reaction medium was then cooled up to 35° C. and decanted in two phases:
  sulfuric phase (152.2 g) with huge crystallization of ammonium mono- and bisulfate. The solid of said phase was washed with 43.1 g of toluene for removing the remaining organic phase.
  organic phase, which contained 74.81 g (0.398 moles) of di-isopropyl malonate, 22.89 g (0.199 moles) of mono-isopropyl malonate and 20.67 g (0.157 moles) of malonic acid, corresponding to a molar yield of 39.8% in di-isopropyl malonate or equivalent to 75.4 molar % in the mixture of malonic acid, the mono-ester and the di-ester. The organic phase contained further: toluene, iso-propyl alcohol, acetic acid, isopropyl acetate, dilsopropyl ether, propene and the ortho- and para- isopropyl toluene.

Up to this point, the mass loss attained 37.54 g due to the non-condensation of the generated propene and to a lesser amount of entrained diisopropyl ether and isopropyl acetate.

The organic phase together with the toluene used to wash the sulfuric phase were then concentrated by distillation for 5 hours resulting in 165.5 g of a distillate which contained 15.8 weight % of isopropyl alcohol, 10.7 weight % of dilsopropyl ether, 39.6 weight % of toluene, 9.8 weight % of isopropyl acetate and small amounts of different products present in the reaction medium.

The mass loss during distillation reached 76.7 g, mainly caused by the non-condensation of propene present in the reaction medium.

In view of the fact that esterification of a portion of the amount of malonic acid and monomalonate proceeded during the concentration step, the final molar yield attained 62.6% in di-isopropyl malonate.

It can be seen that state-of-the-art processes involve successive mass losses which considerably lower the final yield in desired ester.

EXAMPLE 7
Preparation of Dimethyl Malonate:

42.14 g of cyanoacetic acid corresponding to 0.495 moles were charged into a Hastelloy-C autoclave of 1 liter volumetric capacity, then 123.2 g of an aqueous solution of HCl 31.0% (corresponding to 1.05 moles) were added. The reaction was kept under agitation at 400 rpm and heated at a temperature of 75° C. and at an absolute pressure of 1.3 bar. After a 5 hour reaction the mixture of malonic acid and ammonium chloride was isolated according to the procedure described hereinbefore yielding a condensate with the HCl molar excess and 0.50 g acetic acid and 79.5 g of a wet solid which by analysis showed the following composition, by weight:

| Component | Weight % |
|---|---|
| Water | 1.5 |
| Cyanoacetic acid | not found |
| Hydrochloric acid | 1.6 |
| Malonic acid | 63.6 |
| Ammonium chloride | 33.3 |

These results indicate that in the first step the yield in raw malonic acid was 98.3%.

To the above solid were added 106.7 g of methyl alcohol (corresponding to 3,33 moles), the resulting suspension was kept under agitation for 40 minutes for dissolving malonic acid, then the insoluble ammonium chloride was separated by filtering and washed with a further 40 g of methyl alcohol (corresponding to 1.25 moles). The analysis of ammonium chloride did not indicate the presence of malonic acid. The liquid alcoholic streams were then combined and then 7.2 g of concentrated sulfuric acid were added, corresponding to 0.07 moles. Further, 412 g of chloroform were also added, as a co-solvent, then the mixture was transferred to a glass reactor. The reaction was run in a jacketed reactor of 1,000 ml volumetric capacity coupled to a device for distillation under reduced pressure. After heating for half an hour at an internal temperature of 56.4° C. a ternary azeotropic mixture made up of chloroform, methyl alcohol and water began to distill, at a temperature of 53.2° C. The mixture was collected in a decanter. No phase separation was observed in view of the excess methyl alcohol in the reaction medium. That is why it was not necessary to recycle this stream to the esterification reaction in order to complete the esterification of malonic acid. After 2 hours distillation, a further 401.6 g of chloroform were added. When 6 hours reaction were completed a chromatographic analysis test was run, which did not indicate any malonic acid in the medium. The di-methyl malonate-rich reaction medium was then concentrated, at atmospheric pressure. The concentrate was then neutralized with the aid of 158 g of a 5 weight % aqueous solution of sodium carbonate so as to yield two liquid phases which were separated in a decanter. 180 g of aqueous phase were obtained having 0.05 weight % of di-methyl malonate, corresponding to a mass of 0.09 g, which may be recovered by extraction with chloroform and further recycle to the next batch. The efficacy of such procedure for recovering the desired ester product was 97.5%, this corresponding to a recovery of 0.087 g of di-methyl malonate.

The organic phase weighed 102,7 g and had the following composition, by weight:

| Component | Weight % |
|---|---|
| Water | 2.6 |
| Methyl alcohol | 5.6 |
| Chloroform | 38.11 |
| Dimethyl malonate | 57.15 |

Dimethyl malonate was purified by fractional distillation, in batch and under atmospheric pressure, chloroform, methyl alcohol and water being distilled at first. The distillation of the desired ester product occurred at an absolute pressure of 9.3 to 10.6 mbar, the ester distilling at 63–65° C. 57.5 g of dimethyl malonate were obtained of 99.0 mole % purity, the yield based on cyanoacetic acid being 89.8 mole %.

The observations set forth hereinbefore as well as the Examples of the present application are an evidence of the patentably distinguishing aspects of the present process, which render it not suggested not obvious in view of the publications on the subject.

Such distinguishing aspects are:
the hydrolysis of cyanoacetic acid in high yield as a consequence of
the use of hydrochloric acid and resulting low yield in acetic acid by-product;
malonic acid is obtained in admixture to ammonium chloride as a by-product after evaporation of the excess hydrochloric acid and the water present in the reaction medium, malonic acid being separated from the mixture with the aid of a suitable solvent;
evaporation of excess hydrochloric acid so as to recycle it;
the relatively low concentration of the hydrolyzing agent in the reaction medium as a result of its volatility throughout the evaporation for removing water, this leading to high yields;
the malonic acid-alcohol mixture is obtained straight from the concentrated mixture of malonic acid and by-product ammonium chloride by dissolving with an esterifying alcohol, without any need to isolate malonic acid;
in view of the low concentration in mineral acids during the esterification reaction, the process may be successfully applied to secondary alcohols;
the absence of aromatic compounds as contaminants of the malonates in case an aromatic co-solvent is not used to withdraw water formed during the esterification reaction.

What is claimed is:

1. A process for preparing malonic acid through the acid hydrolysis of cyanoacetic acid which comprises the following steps:
a) reacting cyanoacetic acid and at least the stoichiometric amount of aqueous hydrochloric acid, the concentration of said aqueous hydrochloric acid being between 5 and 37 weight %, at a temperature of at least 50° C., for such time as required for the conversion of the reactants, so as to obtain a mixture of malonic acid, ammonium chloride, water, acetic acid by-product and excess hydrochloric acid, if any;

b) separating water, the acetic acid by-product and excess hydrochloric acid by evaporation, so as to obtain a concentrated mixture of malonic acid and ammonium chloride;

c) purifying the concentrated mixture by dissolution with an oxygen-containing organic solvent, the malonic acid product being then separated from the ammonium chloride by-product so as to obtain malonic acid which is then purified and isolated by evaporation of the oxygen-containing organic solvent.

2. A process according to claim 1, wherein the molar ratio of hydrochloric acid to cyanoacetic acid is between 1 and 5.

3. A process according to claim 1 or 2, wherein the concentration of hydrochloric acid is between 10 and 37 weight % and the molar ratio of hydrochloric acid to cyanoacetic acid is between 1.3 and 2.0.

4. A process according to claim 1, wherein the temperature of the reaction of acid hydrolysis is between 60 and 100 ° C.

5. A process according to claim 1, wherein the pressure of the reaction of acid hydrolysis is between 0.5 and 10 bar.

6. A process according to claim 1, whereby the absolute pressure of the evaporation varies between 40 and 1330 mbar.

7. A process according to claim 6, wherein the evaporation is effected in the reactor vessel itself, by heating under reduced pressure.

8. A process according to claim 6, wherein the evaporation is effected in an evaporator.

9. A process according to claim 1, wherein the excess hydrochloric acid is separated and recycled to the process.

10. A process according to claim 1, wherein the oxygen-containing organic solvents used to purify malonic acid in admixture with ammonium chloride comprise $C_3$–$C_8$ ketones, $C_2$–$C_{10}$ acylic ethers, cyclic ethers, $C_2$–$C_6$ esters.

11. A process according to claim 10, wherein the oxygen-containing organic solvents used for purifying malonic acid are evaporated and the malonic acid product is concentrated by crystallization at temperatures between –20 and 35 ° C.

12. A process for preparing malonic acid esters from the acid hydrolysis of cyanoacetic acid which comprises the following steps:

a) reacting cyanoacetic acid and a molar excess of aqueous hydrochloric acid, the concentration of said aqueous hydrochloric acid being between 5 and 37 weight %, at a temperature of at least 50° C., under pressure, for the period of time which is required for the conversion of reactants so as to obtain a mixture of malonic acid, ammonium chloride, water, acetic acid and excess hydrochloric acid which has not reacted;

b) separating water, acetic acid by-product and excess hydrochloric which has not reacted, so as to obtain a concentrated mixture of malonic acid and ammonium chloride;

c) purifying the concentrated mixture of malonic acid and ammonium chloride by dissolution with an esterifying alcohol, the malonic acid and esterifying alcohol mixture being separated from the ammonium chloride by-product;

d) esterifying the malonic acid-esterifying alcohol mixture in the presence of a Brönsted acid catalyst, under heating, and obtaining the corresponding ester;

e) distilling the azeotrope resulting from the formed water and the excess esterifying alcohol, and distilling to concentrate the ester product;

f) neutralizing the concentrated ester product with an inorganic base, and forming an aqueous phase and an organic phase, recovering ester product from the aqueous phase and recycling the recovered ester product to the organic phase;

g) purifying ester product from the organic phase by fractional distillation under reducing pressure, so as to isolate ester product having purity of at least 99 mole %.

13. A process according to claim 12, wherein the esterifying alcohol is a primary and secondary $C_1$–$C_{10}$ alcohol.

14. A process according to claim 13, wherein the esterifying alcohol is methyl alcohol, ethyl alcohol, propyl alcohol, iso-propyl alcohol, n-butyl alcohol, iso-butyl alcohol, sec-butyl alcohol, n-phetyl alcohol, n-hexyl alcohol, iso-hexyl alcohol, n-octyl alcohol, iso-octyl alcohol, 2-ethyl hexyl alcohol, n-decyl alcohol, said alcohol being utilized in a molar ratio of at least 2 moles for each mole of malonic acid.

15. A process according to claim 12, wherein the catalysts for said esterification reaction are selected from the group consisting of chlorosulfonic acid, methanosulfonic acid, p-toluenesulfonic acid, hydrochloric acid, sulfuric acid and similar Bronsted acids, the catalysts being employed in a concentration of between 0.05 moles to 0.5 moles per each mole of malonic acid.

16. A process according to claim 12, wherein a co-solvent is added at the step of azeotrope distillation in order to withdraw the formed water.

17. A process according to claim 12, wherein the esterification reaction is effected at pressures between 67 and 1100 mbar.

18. A process according to claim 8, wherein said evaporation is effected in an evaporator selected from the group consisting of an agitated thin film evaporator, a flash dryer or a spray dryer.

19. A process according to claim 6, wherein said evaporation occurs at a pressure between 133 and 400 mbar.

* * * * *

UNITED STATES PATENT AND TRADEMARK OFFICE
CERTIFICATE OF CORRECTION

PATENT NO. : 6,395,931 B1
DATED : May 28, 2002
INVENTOR(S) : Otavio Vianna Carvalho et al.

It is certified that error appears in the above-identified patent and that said Letters Patent is hereby corrected as shown below:

<u>Title page,</u>
Item [75], Inventors, please correct the name of the last inventor from "Antonio Luiz Ribeiro de Castro" to -- Antonio Luiz Ribeiro de Castro MORSCHBACKER --.

Signed and Sealed this

Twenty-first Day of January, 2003

JAMES E. ROGAN
*Director of the United States Patent and Trademark Office*